(12) United States Patent
Oguchi et al.

(10) Patent No.: US 8,282,910 B2
(45) Date of Patent: Oct. 9, 2012

(54) COMPOSITION FOR SKIN OR HAIR

(75) Inventors: Nozomi Oguchi, Yokohama (JP); Yukie Yoda, Yokohama (JP); Hiroyuki Kakoki, Yokohama (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 343 days.

(21) Appl. No.: 12/528,119

(22) PCT Filed: Feb. 22, 2008

(86) PCT No.: PCT/JP2008/053074
§ 371 (c)(1),
(2), (4) Date: Aug. 21, 2009

(87) PCT Pub. No.: WO2008/102875
PCT Pub. Date: Aug. 28, 2008

(65) Prior Publication Data
US 2010/0008875 A1    Jan. 14, 2010

(30) Foreign Application Priority Data

Feb. 23, 2007 (JP) ................................ 2007-044764

(51) Int. Cl.
| | | |
|---|---|---|
| *A61Q 17/04* | (2006.01) | |
| *A61K 8/49* | (2006.01) | |
| *A61K 8/40* | (2006.01) | |
| *A61K 8/35* | (2006.01) | |

(52) U.S. Cl. ............ 424/59; 424/60; 424/70.9; 514/685
(58) Field of Classification Search ............... 424/59, 424/60, 70.9; 514/685
See application file for complete search history.

(56) References Cited

U.S. PATENT DOCUMENTS

| | | | |
|---|---|---|---|
| 4,457,911 A | 7/1984 | Conner et al. | |
| 4,613,499 A | 9/1986 | Conner | |
| 5,576,354 A | 11/1996 | Deflandre et al. | |
| 5,587,150 A | 12/1996 | Deflandre et al. | |
| 5,624,663 A * | 4/1997 | Deflandre et al. | 424/59 |
| 5,882,634 A | 3/1999 | Allard et al. | |
| 5,951,968 A | 9/1999 | Forestier et al. | |
| 6,033,649 A | 3/2000 | Gonzenbach et al. | |
| 6,224,854 B1 | 5/2001 | Robinson | |
| 6,426,428 B2 | 7/2002 | Forestier et al. | |
| 6,602,515 B2 | 8/2003 | Chaudhuri | |
| 6,831,191 B2 | 12/2004 | Chaudhuri | |
| 7,153,494 B2 * | 12/2006 | Chodorowski-Kimmes et al. | 424/59 |
| 8,025,867 B2 * | 9/2011 | Richard | 424/59 |
| 2002/0016488 A1 | 2/2002 | Forestier et al. | |
| 2006/0104924 A1 | 5/2006 | Candau | |

FOREIGN PATENT DOCUMENTS

| | | |
|---|---|---|
| JP | 59-38273 | 3/1984 |
| JP | 5-504572 | 7/1993 |
| JP | 9-87234 | 3/1997 |
| JP | 9-175974 | 7/1997 |
| JP | 10-175838 | 6/1998 |
| JP | 2000-136120 | 5/2000 |
| JP | 2002-527463 | 8/2002 |
| JP | 2005-503365 | 2/2005 |
| JP | 2006-117669 | 5/2006 |
| JP | 2007-261978 | 10/2007 |

OTHER PUBLICATIONS

Japanese Patent Abstract for Publication No. 09-087234 published Mar. 31, 1997, 18 pages.
Japanese Patent Abstract for Publication No. 2007-261978 published Oct. 11, 2007, 20 pages.
International Report on Patentability for corresponding PCT/JP2008/053074 mailed Sep. 11, 2009, seven pages.
International Search Report for corresponding PCT/JP2008/053074 mailed May 1, 2008, three pages.

* cited by examiner

*Primary Examiner* — Mina Haghighatian
(74) *Attorney, Agent, or Firm* — Rankin, Hill & Clark LLP

(57) ABSTRACT

The present invention provides a composition for skin or hair which achieves an excellent UV absorption in a wide range of UV wavelength from the UV-A to the UV-B without inhibiting the effect of the alkyl β,β-diphenylacrylate and the α-cyano-β,β-diphenylacrylate (e.g. octocrylene) which serve to improve the photostability of dibenzoylmethane derivative. The composition for skin or hair comprises: (a) a dibenzoylmethane derivative, (b) an alkyl β,β-diphenylacrylate and/or an α-cyano-β,β-diphenylacrylate (e.g. octocrylene), and (c) a specific benzalmalonate derivative (e.g. di(2-ethylhexyl)-4-methoxybenzalmalonate).

13 Claims, 1 Drawing Sheet

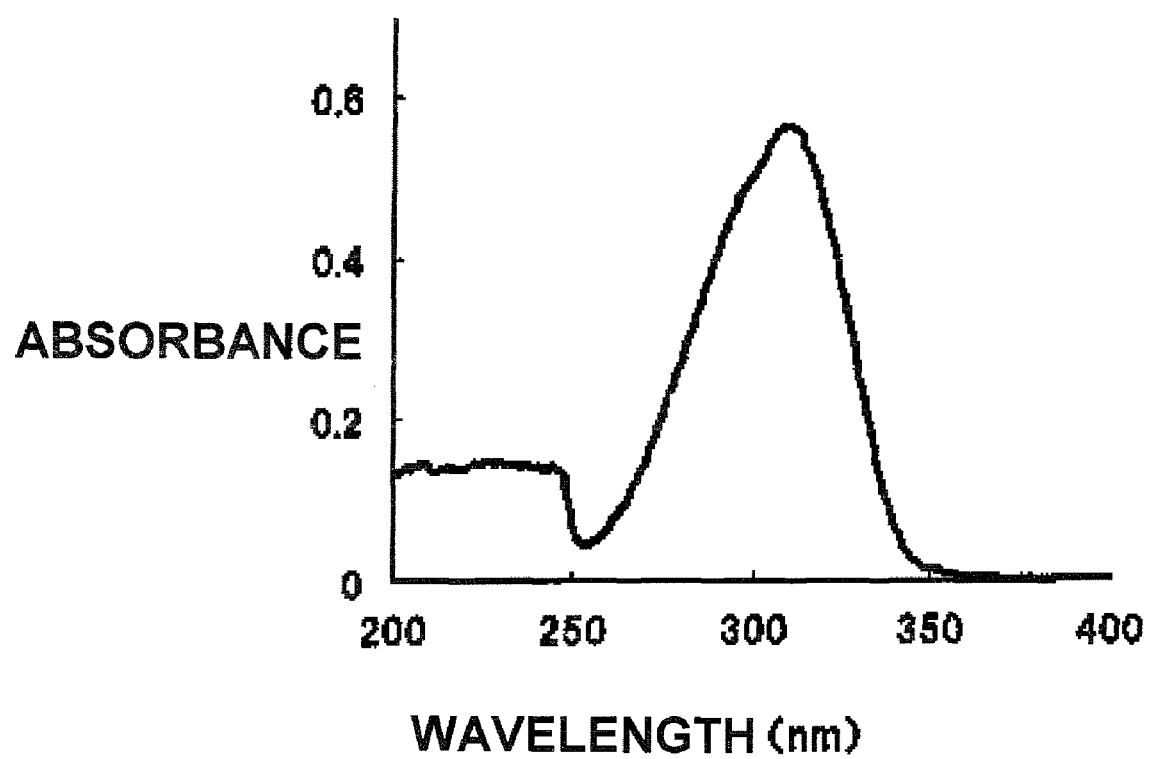

COMPOSITION FOR SKIN OR HAIR

RELATED APPLICATIONS

This application claims the priority of Japanese Patent Application No. 2007-44764 filed on Feb. 23, 2007, which is incorporated herein by reference.

FIELD OF THE INVENTION

The present invention relates to a composition for external use on skin or hair. Particularly, the present invention relates to the composition for skin or hair which achieves a highly excellent stability (photostability) and an excellent UV absorption over a wide UV wavelength range from UV-A to UV-B. The present invention is preferably applied to sunscreen cosmetics.

BACKGROUND OF THE INVENTION

UV absorbers are blended in cosmetics to protect human skin from UV radiation or to prevent degradation of components due to UV rays.

The UV wavelength range can be divided into UV-A (320 to 400 nm), UV-B (290 to 320 nm), and UV-C (up to 290 nm). Among them, UV-C ray generally does not reach the earth's surface.

UV-A ray (320 to 400 nm) has not been thought to accelerate skin aging by causing sunburn such as UV-B ray (290 to 320 nm) though it blackens the skin. Recently, however, it has been revealed that UV-A ray reaches deep into the skin and causes not only skin aging but it also promotes the formation of skin cancer while UV-B ray only reaches relatively surface layers of the skin.

When classifying according to molecular structure, conventional UV absorbers for cosmetics can be classified into (1) benzoic acid derivative, (2) cinnamate derivative, (3) benzophenone derivative, (4) dibenzoylmethane derivative, (5) salicylic acid derivative, (6) camphor derivative, (7) phenylbenzimidazole derivative, (8) phenylbenzotriazole derivative, (9) triazine derivative, (10) phenyl acrylate derivative, and so on.

Among the above-mentioned absorbers, (4) dibenzoylmethane derivative is one of the most widely used UV absorbers in cosmetic field in recent years because it is excellent in safety and UV absorbing ability (especially UV-A absorbing ability). One of the representative examples of dibenzoylmethane derivative is 4-tert-butyl-4'-methoxydibenzoylmethane which is the most used UV-A absorber because it has absorption maximum around 360 nm as well as a large absorbance and is excellent in absorbing UV-A ray.

However, the dibenzoylmethane derivative has a low photostability. Therefore, a preparation containing dibenzoylmethane derivative has had a problem in that its UV protective effect is deteriorated over time by exposure to UV ray or sunlight. Thus, in order to exert a constant skin protecting effect for many hours under light, it was necessary to apply the preparation containing dibenzoylmethane derivative to the skin or hair steady or repeatedly within a short period of time.

To try to solve the above-mentioned problem, Patent Literatures 1 and 2 disclose that certain kinds of alkyl β,β-diphenylacrylate and α-cyano-β,β-diphenylacrylate, which are used as UV absorbers, improve photostability of the dibenzoylmethane derivative. For details, Patent Literature 1 discloses a light-blocking cosmetic composition which stabilizes the UV-A blocking agent by blending the UV-A blocking agent (such as dibenzoylmethane derivative) with an alkyl β,β-diphenylacrylate or an α-cyano-β,β-diphenylacrylate in a specific proportion. Patent Literature 2 discloses a light-blocking cosmetic composition with photostability which is prepared by blending a benzoylmethane-type UV-A blocking agent with a α-cyano-β,β-diphenylacrylate stabilizer in a specific proportion to stabilize the benzoylmethane-type UV-A blocking agent and adding arbitrarily at least one kind of general UV-B filter. In Patent Literature 2, a particulate pigment (e.g. a micro pigment of a general metal oxide) is specified as the above-mentioned UV-B filter.

However, there has been a problem in that the effect of the alkyl β,β-diphenylacrylate and the α-cyano-β,β-diphenylacrylate to stabilize a dibenzoylmethane derivative is inhibited by blending a cinnamate derivative (such as octyl methoxycinnamate), which is one of the widely used UV absorbers in cosmetics, especially as a UV-B absorber, into a system using a dibenzoylmethane derivative as disclosed in the Patent Literatures in combination with alkyl β,β-diphenylacrylate or α-cyano-β,β-diphenylacrylate.

If it is possible to blend a UV-B absorber having an excellent UV absorption (especially for UV-B ray) into a system containing a dibenzoylmethane derivative (i.e. UV-A agent) and an alkyl β,β-diphenylacrylate, α-cyano-β,β-diphenylacrylate and similar stabilizers (i.e. stabilizers capable of enhancing photostability of the dibenzoylmethane derivative) without deteriorating the effect of the alkyl β,β-diphenylacrylate and similar stabilizers to photostabilize the dibenzoylmethane derivative, a UV absorption for a wide range of UV wavelength from the UV-A ray to the UV-B ray can be achieved stably. The development of such products has been desired.

As far as known to the inventors of the present invention, there has been no literature specifically disclosing the way to solve the problem in that the use of cinnamate derivatives inhibits the effect of the alkyl β,β-diphenylacrylate and the α-cyano-β,β-diphenylacrylate on the stabilization of dibenzoylmethane derivatives.

[Patent literature 1] Japanese Patent No. 2975682
[Patent literature 2] Japanese Unexamined Patent Publication H09-175974

DISCLOSURE OF THE INVENTION

Problem to be Solved by the Invention

The present invention has been conceived in light of the above-described problems, and its purpose is to provide a composition for skin or hair which can stably blend several kinds of poorly-soluble UV absorbers so as to provide high solubility and achieve an excellent UV absorption in a wide range of UV wavelength from the UV-A to the UV-B without inhibiting the effect of the alkyl β,β-diphenylacrylate and/or the α-cyano-β,β-diphenylacrylate that serve to improve photostability of the dibenzoylmethane derivative.

Means to Solve the Problem

As a result of extensive investigation to solve the problems described above, the inventors of the present invention found that blending a specific benzalmalonate derivative into a system containing a dibenzoylmethane derivative and an alkyl β,β-diphenylacrylate and/or an α-cyano-β,β-diphenylacrylate enhances the UV protective effect and enables the composition to be blended with several kinds of poorly-soluble UV absorbers and it provides a high solubility without inhibiting the effect of the alkyl β,β-diphenylacrylate or the α-cyano-β,β-diphenylacrylate to photostabilize the dibenzoyl-methane derivative, which resulted in completion of the present invention.

The present invention provides a composition for skin or hair comprising;
(a) a dibenzoylmethane derivative,
(b) an alkyl β,β-diphenylacrylate and/or α-cyano-β,β-diphenylacrylate, and
(c) a benzalmalonate derivative represented by the following formula (I):

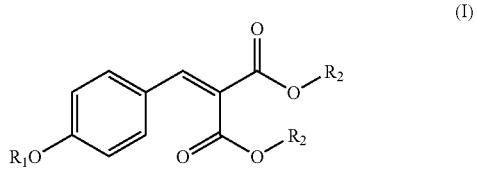

wherein, $R_1$ and $R_2$ independently represent an alkyl group having a carbon number of 1 to 20.

The present invention provides the composition for skin or hair, wherein $R_1$ in the above-mentioned formula (I) is a methyl group.

The present invention provides the composition for skin or hair, wherein $R_2$ in the above-mentioned formula (I) is a 2-ethylhexyl group.

The present invention provides the composition for skin or hair comprising 0.1% by mass or more of component (c).

The present invention provides the composition for skin or hair, wherein component (a) is 4-tert-butyl-4'-methoxydibenzoylmethane.

The present invention provides the composition for skin or hair, wherein component (b) is octocrylene.

The present invention provides the composition for skin or hair comprising 0.01 to 10% by mass of component (a).

The present invention provides the composition for skin or hair comprising 0.01 to 10% by mass of component (b).

The present invention provides the composition for skin or hair, which is a sunscreen cosmetic.

Effect of the Invention

According to the present invention, a composition which enhances the UV protective effect and has an excellent sustainability of UV absorption of the dibenzoylmethane derivative and the benzalmalonate derivative while preserving the photostability of the dibenzoylmethane derivative improved by the alkyl β,β-diphenylacrylate and/or the α-cyano-β,β-diphenylacrylate, can be obtained by using a specific benzalmalonate derivative in combination with the dibenzoylmethane derivative and the alkyl β,β-diphenylacrylate and/or the α-cyano-β,β-diphenylacrylate.

BRIEF DESCRIPTION OF THE DRAWINGS

FIG. 1 is a graph showing an absorbance of the compound obtained in Synthesis Example 1, that is, di(2-ethylhexyl)-4-methoxybenzalmalonate represented in formula (II).

DESCRIPTION OF THE PREFERRED EMBODIMENT

The present invention will be further detailed in the following.

For component (a), one or more kinds of dibenzoylmethane derivatives known as UV absorbers are used. In the present invention, 4-tert-butyl-4'-methoxydibenzoylmethane is particularly preferred. 4-tert-butyl-4'-methoxydibenzoyl-methane is, for example, commercially available from DSM Nutritional Products, Inc. under the commercial name of "Parsol 1789", which can be used in the present invention.

The blending amount of component (a) is preferably from 0.01 to 10% by mass with respect to the composition of the present invention, more preferably from 0.3 to 5% by mass. If the blending amount of component (a) is less than 0.01% by mass, it is difficult to achieve a sufficient UV absorption. On the other hand, for cosmetics or preparations for external use on skin, 10% by mass of component (a) is enough to achieve a sufficient UV absorption. If component (a) is blended in the amount of more than 10% by mass, the effect is not improved in proportion to the increase of blending amount, which is not economical.

Component (b) is an alkyl β,β-diphenylacrylate and/or an α-cyano-β,β-diphenylacrylate known as a UV absorber. Between them, an α-cyano-β,β-diphenylacrylate is preferred. In the present invention, octocrylene (that is 2-ethylhexyl 2-cyano-3,3'-diphenylacrylate) is particularly preferred. For example, octocrylene is commercially available under the commercial name of "Parsol 340" (DSM Nutritional Products, Inc.), "Uvinul N 539 T" (BASF Corporation), "Neo Heliopan, Type 303" (Symrise), "Eusolex OCR" (EMD Chemicals Inc.), "Escalol 597" (International Specialty Products), and so on, which can be used in the present invention.

The blending amount of component (b) is preferably from 0.01 to 10% by mass with respect to the composition of the present invention, more preferably from 0.3 to 5% by mass. If the blending amount of component (b) is less than 0.01% by mass, it is difficult to achieve a sufficient UV absorption. On the other hand, if it exceeds 10% by mass, there is a tendency of sticky feeling in use.

Component (c) is a benzalmalonate derivative represented by the following formula (I):

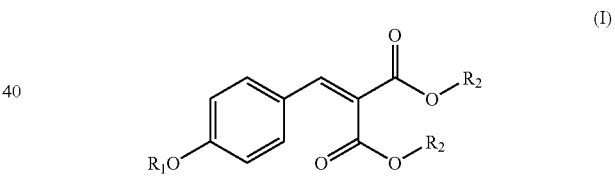

In the above formula (I), $R_1$ and $R_2$ independently represent an alkyl group having a carbon number of 1 to 20.)

In the present invention, it is particularly preferred that $R_1$ is a methyl group. For $R_2$, 2-ethylhexyl group is preferred. Thus, for component (c) in the present invention, di(2-ethylhexyl)-4-methoxybenzalmalonate represented by the following formula (II) is particularly preferred.

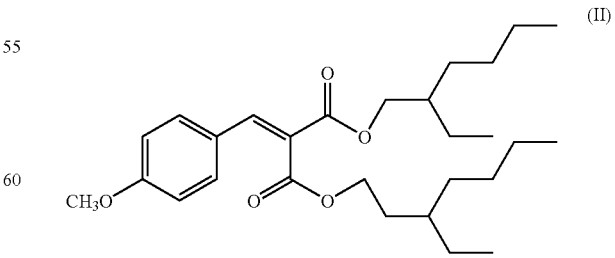

For example, component (c) can be synthesized by Knoevenagel condensation using p-alkoxy-substituted benzaldehyde (formula (III)) and malonic acid dialkyl ester (formula (IV)) as explained in the following Scheme (1). In Scheme (1), $R_1$ and $R_2$ are as defined in the above-mentioned formula (I).

<Scheme (1)>:

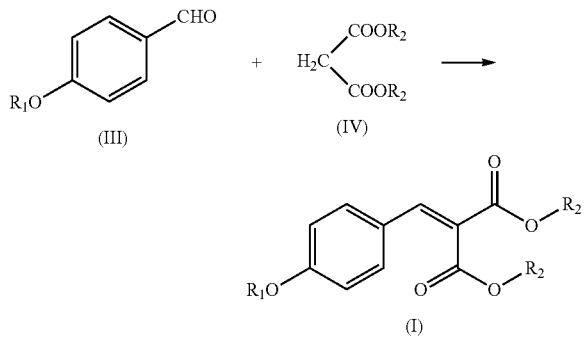

This reaction can be executed in a solvent such as aromatic hydrocarbons (e.g. benzene, toluene, and xylene); tetrahydrofuran; dioxane; and alcohol; at a temperature from room temperature to the reflux temperature of the solvent in the presence of catalyst. Examples of the catalyst include bases such as piperidine and pyridine; acids such as acetic acid, benzoic acid, zinc chloride, and titanium tetrachloride; carboxylate such as sodium acetate and ammonium acetate; and acid anhydride such as acetic anhydride.

<Scheme (2)>:

Malonic acid dialkyl ester (formula (IV)) can be obtained, for example, by esterification reaction of malonic acid with the corresponding alcohol $R_2OH$.

The blending amount of component (c) is not particularly restricted as long as it does not deteriorate the effect of the composition in which component (b) improves the photostability of component (a) and it is present in sufficient quantities to maintain the UV absorption properties of component (c). The minimal amount of component (c) for photostabilization can be determined by a general measurement test for photostability, and typically, it is 0.1% by mass or more with respect to the composition, more preferably 0.5% by mass or more. The upper limit amount of component (c) is not particularly restricted, and 10% by mass with respect to the composition is preferred. If the blending amount of component (c) is less than 0.1% by mass, it is difficult to achieve a sufficient UV absorption of component (c). On the other hand, for cosmetics or preparations for external use on skin, 10% by mass of component (c) is enough to achieve a sufficient UV absorption. If component (c) is blended in the amount of more than 10% by mass, the effect is not improved in proportion to the increase of blending amount, which is not economical.

In the composition of the present invention, in addition to the above-mentioned essential components, water-soluble or oil-soluble UV absorbers can be further blended arbitrarily within the range where the effect of the present invention is not deteriorated.

Examples of such a UV absorber includes triazine UV absorbers (such as bis(resorcinyl)triazine, 2,4-bis{[4-(2-ethylhexyloxy)-2-hydroxy]-phenyl}-6-(4-methoxyphenyl)-1,3,5-triazine), and octyl triazone (2,4,6-tris-[4-(2-ethylhexyloxycarbonyl)anilino]-1,3,5-triazine); benzoic acid UV absorbers (such as p-aminobenzoic acid (hereinafter abbreviated as "PABA"), PABA monoglycerin ester, N,N-dipropoxy PABA ethyl ester, N,N-diethoxy PABA ethyl ester, N,N-dimethyl PABA ethyl ester, and N,N-dimethyl PABA ethyl ester); anthranilic acid UV absorbers (such as homomenthyl-N-acetyl anthranilate); salicylic acid UV absorbers (such as amyl salicylate, menthyl salicylate, homomenthyl salicylate, octyl salicylate, phenyl salicylate, benzyl salicylate, and p-isopropanol phenyl salicylate); cinnamic acid UV absorbers (such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, 2-ethylhexyl p-methoxycinnamate, 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, glyceryl mono-2-ethyl hexanoyl-dipara methoxycinnamate, and diethanoleamine ethoxycinnamate); benzophenone UV absorbers (such as 2-[4-(diethylamino)-2-hydroxybenzoyl]-benzoic acid hexyl ester, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,1-camphor; 3-benzylidene-d,1-camphor; 2-phenyl-5-methyl benzoxazole; 2,2'-hydroxy-5-methylphenyl benzotriazole; 2-(2'-hydroxy-5'-t-octylphenyl)benzotriazole; 2-(2'-hydroxy-5'-methylphenyl)benzotriazole; dibenzaladine; dianisoylmethane; 5-(3,3-dimethyl-2-norbornylidene)-3-pentane-2-one; phenyl acrylate UV absorbers (such as 2-ethylhexyl-2-cyano-3,3-diphenylacrylate and ethyl-2-cyano-3,3-diphenylacrylate); phenylbenzimidazole derivatives (such as phenylbenzimidazole sulfonic acid and disodiumphenyldibenzimidazole tetrasulfonate); camphor derivatives (such as 4-methylbenzylidene camphor and terephthalylidene dicamphor sulfonic acid); phenylbenzotriazole derivatives (such as hydroxy-(ethylhexyl)-phenoxy benzotriazole, and methylene bis-benzotriazolyl tetramethylbutylphenol); and benzalmalonate derivatives (such as dimethicone benzalmalonate).

Preferably, among the above-mentioned UV absorbers, the composition of the present invention further comprises one or more selected from the group consisting of cinnamate derivatives, anthranilate derivatives, salicylic acid derivatives, camphor derivatives, benzalmalonate derivatives, benzimidazole derivatives, p-aminobenzoic acid derivatives, methylene bis (hydroxyphenyl)benzotriazol derivatives, and triazine derivatives; more preferably, ethylhexyl salicylate, homosalate, 2-ethylhexyl p-methoxycinnamate (2-ethylhexyl p-methoxysilicate), octocrylene, phenylbenzimidazole sulfonic acid, 4-methylbenzylidene camphor, methylene bis-benzotriazolyl tetramethylbutylphenol, phenylbenzotriazole, diethylamino hydroxybenzoyl benzoic acid hexyl ester, hydroxy-(ethylhexyl)phenoxybenzotriazol, bis-ethylhexyl phenol methoxyphenyltriazine, dimethicone diethyl benzalmalonate, and disodiumphenyldibenzimidazole tetrasulfonate.

Additionally, as necessary, other components generally used in external preparations can be further blended arbitrarily in the composition of the present invention as long as the effect of the present invention is not deteriorated; the examples of other components include powder components, liquid oils, solid oils, waxes, hydrocarbons, higher fatty acids, higher alcohols, esters, silicones, anionic surfactants, cationic surfactants, amphoteric surfactants, nonionic surfactants, moisturizers, water-soluble polymers, thickeners, coating agents, metal ion sequestering agents, lower alcohols, polyhydric alcohols, saccharides, amino acids, organic amines, polymer emulsions, pH adjusters, skin nutrients, vitamins, antioxidants, antioxidant aids, perfumes, and water. The composition of the present invention can be prepared by normal preparation methods depending on a desired product form.

Examples of powder components include inorganic powders (such as talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, calcined calcium sulfate (calcined gypsum), calcium phosphate, fluorine apatite, hydroxy apatite, ceramic powder, metallic soaps (for example, zinc myristate, calcium palmitate, and aluminum stearate), and boron nitride); organic powders (such as polyamide resin powder (nylon powder), polyethylene powder, poly methyl methacrylate powder, polystyrene powder, styrene/acrylic acid copolymer resin powder, benzoguanamine resin powder, polytetrafluoroethylene powder, and cellulose powder); inorganic white pigments (such as titanium dioxide and zinc oxide); inorganic red pigments (such as iron oxide (red iron oxide) and iron titanate); inorganic brown pigments (such as γ-iron oxide); inorganic yellow pigments (such as yellow iron oxide and ocher); inorganic black pigments (such as black iron oxide and low oxides of titanium); inorganic purple pigments (such as manganese violet and cobalt violet); inorganic green pigments (such as chromium oxide, chromium hydroxide, and cobalt titanate); inorganic blue pigments (such as ultramarine blue and Berlin blue); pearl pigment (such as titanium oxide coated mica, titanium oxide coated bismuth oxychloride, titanium oxide coated talc, colored titanium oxide coated mica, bismuth oxychloride, and fish scale flakes); metal powder pigments (such as aluminum powder and copper powder); organic pigments such as zirconium, barium or aluminum rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1); and natural colors (such as chlorophyll and β-carotene).

Examples of liquid oil include avocado oil, camellia oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japanese tung oil, jojoba oil, germ oil, and triglycerin.

Examples of solid oil include cacao butter, coconut oil, horse fat, hardened coconut oil, palm oil, beef tallow, mutton tallow, hardened beef tallow, palm kernel oil, pork tallow, beef bone tallow, Japan wax kernel oil, hardened oil, heatsfoot oil, Japan wax, and hardened castor oil.

Examples of waxes include beeswax, candelilla wax, cotton wax, carnauba wax, bayberry wax, Chinese wax, spermacetim, montan wax, rice bran wax, lanolin, kapok wax, lanolin acetate, liquid lanolin, sugar cane wax, isopropyl lanolate, hexyl laurate, reduced lanolin, jojoba wax, hard lanolin, shellac wax, POE lanoline alcohol ether, POE lanoline alcohol acetate, POE cholesterol ether, lanolin fatty acid polyethylene glycol, and POE hydrogenated lanolin alcohol ether.

Examples of hydrocarbon oils include liquid paraffin, ozokerite, squalane, pristane, paraffin, ceresin, squalene, petrolatum, and microcrystalline wax.

Examples of higher fatty acids include lauric acid, myristic acid, palmitic acid, stearic acid, behenic acid, oleic acid, undecylenic acid, tolic acid, isostearic acid, linoleic acid, linolenic acid, eicosapentaenoic acid (EPA), and docosahexaenoic acid (DHA).

Examples of higher alcohols include linear alcohol (such as lauryl alcohol, cetyl alcohol, stearyl alcohol, behenyl alcohol, myristyl alcohol, oleyl alcohol, and cetostearyl alcohol); branched-chain alcohol (such as monostearyl glycerin ether (batylalcohol), 2-decyltetradecynol, lanolin alcohol, cholesterol, phytosterol, hexyldodecanol, isostearyl alcohol, and octyldodecanol).

Examples of synthetic ester oils include tripropylene glycol dineopentanoate, isononyl isononate, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentylglycol dicaprate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri(2-ethylhexanoate), glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, 2-octyldodecyl ester N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oil include linear polysiloxanes (such as dimethylpolysiloxane, methylphenylpolysiloxane, and diphenylpolysiloxane); cyclic polysiloxanes (such as octamethylcyclotetrasiloxane, decamethylcyclopentasiloxane, and dodecamethylcyclohexasiloxane); silicon resin forming three-dimensional network structure; silicone rubber; and various kinds of modified polysiloxane (such as amino modified polysiloxane, polyether modified polysiloxane, alkyl modified polysiloxane, and fluorine modified polysiloxane).

Examples of anionic surfactant include fatty acid soap (such as sodium laurate and sodium palmitate); higher alkyl sulfuric ester salts (such as sodium lauryl sulfate and potassium lauryl sulfate); alkyl ether sulfuric ester salts (such as triethanolamine POE lauryl sulfate and sodium POE lauryl sulfate); N-acyl sarcosinic acids (such as sodium lauroyl sarcosinate); higher fatty acid amide sulfonate (such as sodium N-myristoyl-N-methyltaurine, sodium coconut oil fatty acid methyltauride, and sodium laurylmethyltauride); phosphoric ester salts (such as sodium POE oleyl ether phosphate and POE stearyl ether phosphate); sulfosuccinates (such as sodium di-2-ethylhexyl sulfosuccinate, sodium monolauroylmonoethanolamide polyoxyethylene sulfosuccinate, and sodium lauryl polypropylene glycol sulfosuccinate); alkylbenzene sulfonates (such as sodium linear dodecylbenzenesulfonate, triethanolamine linear dodecylbenzenesulfonate, and linear dodecylbenzenesulfonic acid); higher fatty acid ester sulfate ester salts (such as sodium hardened coconut oil fatty acid glycerol sulfate); N-acylglutamates (such as monosodium N-lauroylglutamate, disodium N-stearoylglutamate, and monosodium N-myristoyl-L-glutamate); sulfated oils (such as Turkey red oil); POE-alkyl ether carboxylic acids; POE-alkyl aryl ether carboxylates; α-olefin sulfonates; higher fatty acid ester sulfonates; secondary alcohol sulfuric acid ester salts; higher fatty acid alkylolamide sulfuric acid ester salts; sodium lauroyl monoethanolamide succinate; ditriethanolamine N-palmitoyl aspartate; and sodium casein.

Examples of cationic surfactant include alkyltrimethylammonium salts (such as stearyltrimethylammonium chloride and lauryltrimethylammonium chloride); alkylpyridinium salts (such as cetylpyridinium chloride); distearyldimethylammonium chloride; dialkyldimethylammonium salts; poly (N,N'-dimethyl-3,5-methylenepiperidinium) chloride; alkyl quaternary ammonium salts; alkyldimethylbenzylammonium salts; alkylisoquinolinium salts; dialkylmorpholinium salts; POE-alkylamines; alkylamine salts; polyamine fatty acid derivatives; amyl alcohol fatty acid derivatives; benzalkonium chloride; and benzethonium chloride.

Examples of amphoteric surfactant include imidazoline amphoteric surfactants (such as sodium 2-undecyl-N,N,N-(hydroxyethylcarboxymethyl)-2-imidazoline and disodium 2-cocoyl-2-imidazolinium hydroxide-1-carboxyethyloxy); and betaine surfactants (such as 2-heptadecyl-N-carboxymethyl-N-hydroxyethylimidazolinium betaines, lauryldimethylaminoacetic acid betaines, alkyl betaines, amide betaines, and sulfo betaines).

Examples of lipophilic nonionic surfactant include sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerol or polyglycerol fatty acid esters (such as glycerol mono-cotton seed oil fatty acid ester, glycerol monoerucate, glycerol sesquioleate, glycerol monostearate, glycerol α,α'-oleate pyroglutamate, and glycerol monostearate malate); propylene glycol fatty acid esters (such as propylene glycol monostearate); hardened castor oil derivatives; and glycerol alkyl ethers.

Examples of hydrophilic nonionic surfactant include POE-sorbitan fatty acid esters (such as POE-sorbitan monooleate, POE-sorbitan monostearate, and POE-sorbitan tetraoleate); POE sorbitol fatty acid esters (such as POE-sorbitol monolaurate, POE-sorbitol monooleate, POE-sorbitol pentaoleate, and POE sorbitol monostearate); POE-glycerol fatty acid esters (e.g. POE-monooleates such as POE-glycerol monostearate, POE-glycerol monoisostearate, and POE-glycerol triisostearate); POE-fatty acid esters (such as POE-distearate, POE-monodioleate, and ethylene glycol distearate); POE-alkyl ethers (such as POE-lauryl ether, POE-oleyl ether, POE-stearyl ether, POE-behenyl ether, POE-2-octyldodecyl ether, and POE-cholestanol ether); Pluronic type surfactants (such as Pluronic); POE/POP-alkyl ethers (such as POE/POP cetyl ether, POE/POP 2-decyltetradecyl ether, POE/POP monobutyl ether, POE/POP hydrogenated lanolin, and POE/POP glycerol ether); tetraPOE/tetraPOP-ethylenediamine condensates (such as Tetronic); POE-castor oil or hardened castor oil derivatives (such as POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate); POE-beeswax lanolin derivatives (such as POE-sorbitol beeswax); alkanolamides (such as coconut oil fatty acid diethanolamide, lauric acid monoethanolamide, and fatty acid isopropanolamide); POE-propylene glycol fatty acid esters; POE-alkylamines; POE-fatty acid amides; sucrose fatty acid esters; alkylethoxydimethylamine oxides; and trioleyl phosphate.

Examples of moisturizer include polyethylene glycol, propylene glycol, glycerin, 1,3-butylene glycol, xylitol, sorbitol, maltitol, chondroitin sulfate, hyaluronic acid, mucoitin sulfate, charonin acid, atelocollagen, cholesteryl 12-hydroxystearate, sodium lactate, bile acid salts, dl-pyrrolidonecarboxylic acid salts, short-chain soluble collagen, diglycerol (EO) PO adducts, chestnut rose (*R. roxburghii plena*) extract, yarrow (*Achillea millefolium*) extract, and melilot extract.

Examples of natural water-soluble polymer include plant-derived polymers (such as gum arabic, tragacanth gum, galactan, guar gum, carob gum, gum karaya, carrageenan, pectin, agar, quince seed (quince), algae colloid (brown algae extract), starch (rice, corn, potato, and wheat), and glycyrrhizinate); microorganism-derived polymers (such as xanthan gum, dextran, succinoglucan, and pullulan); and animal-derived polymers (such as collagen, casein, albumin, and gelatin.)

Examples of semi-synthetic water-soluble polymer include starch polymers (such as carboxymethyl starch and methylhydroxypropyl starch); cellulose polymers (such as methyl cellulose, ethyl cellulose, methylhydroxypropyl cellulose, hydroxyethyl cellulose, sodium cellulose sulfate, hydroxypropyl cellulose, carboxymethyl cellulose, sodium carboxymethyl cellulose, crystalline cellulose, and cellulose powder); and alginate polymers (such as sodium alginate and propylene glycol alginate.)

Examples of synthetic water-soluble polymer include vinyl polymers (such as polyvinyl alcohol, polyvinyl methyl ether, polyvinylpyrrolidone, and carboxyvinyl polymer); polyoxyethylene polymers (such as polyoxyethylene/polyoxypropylene copolymers, for example, polyethylene glycol 20,000, 40,000 or 60,000); acrylic polymers (such as sodium polyacrylate, polyethyl acrylate and polyacrylamide); polyethyleneimine; and cationic polymers.

Examples of thickener include gum arabic, carrageenan, gum karaya, tragacanth gum, carob gum, quince seed (quince), casein, dextrin, gelatin, sodium pectate, sodium alginate, methyl cellulose, ethyl cellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyldimethylammonium sulfate cellulose, xanthan gum, aluminum magnesium silicate, bentonite, hectorite, aluminum magnesium silicate (bee gum), Laponite, and silicic anhydride.

Examples of sequestering agent include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium hydroxyethyl ethylenediamine triacetate.

Examples of lower alcohol include ethanol, propanol, isopropanol, isobutyl alcohol, and t-butyl alcohol.

Examples of polyhydric alcohol include dihydric alcohols (such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (such as glycerin and trimethylolpropane); tetrahydric alcohols (such as pentaerythritol, for example, 1,2,6-hexanetriol); pentahydric alcohols (such as xylitol); hexahydric alcohols (such as sorbitol and mannitol); polyhydric alcohol polymers (such as diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkyl ethers (such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerol monoalkyl ethers (such as chimyl alcohol, selachyl alcohol, and batyl alcohol); sugar alcohols (such as sorbitol, maltitol, maltotriose, mannitol, sucrose, erythritol, glucose, fructose, starch-degraded sugars, maltose, xylitose, and reduction alcohols of starch-degraded sugars); glysolid; tetrahydrofurfuryl alcohol; POE-tetrahydrofurfuryl alcohol; POP-butyl ether; POP/POE-butyl ether; tripolyoxypropylene glycerin ether; POP-glycerol ether; POP-glycerin ether phosphate; POP/POE-pentaerythritol ether; and polyglycerol.

Examples of monosaccharides include trioses (such as D-glycerylaldehyde and dihydroxyacetone); tetroses (such as D-erythrose, D-erythrulose, D-threose, and erythritol); pentoses (such as L-arabinose, D-xylose, L-lyxose, D-arabinose, D-ribose, D-riburose, D-xylulose, and L-xylulose); hexoses (such as D-glucose, D-talose, D-psicose, D-galactose, D-fructose, L-galactose, L-mannose, and D-tagatose); heptoses (such as aldoheptose and heptulose); octoses (such as octulose); deoxysugars (such as 2-deoxy-D-ribose, 6-deoxy-L-galactose, and 6-deoxy-L-mannose); amino sugars (such as D-glucosamine, D-galactosamine, sialic acid, aminouronic acid, and muramic acid); and uronic acids (such as D-glucuronic acid, D-mannuronic acid, L-guluronic acid, D-galacturonic acid, and L-iduronic acid).

Examples of oligosaccharides include sucrose, gentianose, umbelliferose, lactose, planteose, isolychnoses, α,α-threhalose, raffinose, lychnoses, umbilicin, and stachyose verbascoses.

Examples of polysaccharides include cellulose, quince seed, chondroitin sulfate, starch, galactan, dermatan sulfate, glycogen, gum arabic, heparan sulfate, hyaluronic acid, tragacanth gum, keratan sulfate, chondroitin, xanthan gum, mucoitin sulfate, guar gum, dextran, keratosufate, locust bean gum, succinoglucan, and caronic acid.

Examples of amino acid include neutral amino acids (such as threonine and cysteine); acidic amino acids (such as hydroxylysine). In addition, examples of amino acid derivative include sodium acylsarcosinates (sodium lauroylsarcosinate), acylglutamic acid salts, sodium acyl-β-alanine, glutathione, and pyrrolidonecarboxylic acid.

Examples of organic amine include monoethanolamine, diethanolamine, triethanolamine, morpholine, triisopropanolamine, 2-amino-2-methyl-1,3-propanediol, and 2-amino-2-methyl-1-propanol.

Examples of polymer emulsion include acrylic resin emulsions, polyethyl acrylate emulsions, acrylic resin solutions, polyacryl alkyl ester emulsions, polyvinyl acetate resin emulsions, and natural rubber latex.

Examples of vitamin include vitamins A, $B_1$, $B_2$, $B_6$, C, E and their derivatives, pantothenic acid and its derivatives, and biotin.

Examples of antioxidant include tocopherols, dibutylhydroxytoluene, butylhydroxyanisole, and gallic acid esters.

Examples of antioxidant aid include phosphoric acid, citric acid, ascorbic acid, maleic acid, malonic acid, succinic acid, fumaric acid, cephalin, hexametaphosphates, phytic acid, and ethylenediaminetetraacetic acid.

Examples of other possible components to be blended include antiseptic (such as ethylparaben and butylparaben); antiphlogistic (such as glycyrrhizic acid derivatives, glycyrrhetinic acid derivatives, salicylic acid derivatives, hinokitiol, zinc oxide, and allantoin); whitening agent (such as placenta extract, *saxifrage sarmentosa* extract, and arbutin); various extracts (such as *phellodendron* bark, goldthread, *lithospermum* root, *paeonia albiflora, swertia japonica*, birch, sage, loquat, carrot, aloe, *malva sylvestris* (mallow), iris, *vitis vinifera* (grape), *coix lacryma-jobi* (job's tears), *luffa cylindrica*, lily, saffron, *cnidium officinale*, ginger, *hypericum perforatum, ononis spinosa, allium sativum* (gerlic), *capsicum frutescens, citrus unshiu* peel, *angelica acutiloba*, and sea alga); activator agent (for example, royal jelly, photosensitizers, and cholesterol derivatives); blood circulation accelerator (such as nonylic acid vanillylamide, nicotinic acid benzyl esters, nicotinic acid β-butoxy ethyl esters, capsaicin, Zingerone, Cantharides tincture, ichthammol, tannic acid, α-borneol, tocopherol nicotinate, inositol hexanicotinate, cyclandelate, cinnarizine, tolazoline, acetylcholine, verapamil, cepharanthine, and γ-orizanol); antiseborrheic agent (such as sulfur and thianthol); and anti-inflammatory agent (such as tranexamic acid, thiotaurine, and hypotaurine).

The composition for external use of the present invention can take any form such as a solubilized form, an emulsified form, a suspended form, a liquid form, a solid form, a semi-solid form, a gel form, an ointment form, or any other form.

In addition, the composition for external use of the present invention can be used in any products including external preparations for facial use such as lotions, emulsions, creams, and packs; external preparations for makeup use such as foundations, lipsticks, and eye shadows; external preparations for body use; aromatic compositions; skin cleansing preparations such as makeup removers and body shampoo; ointments; external preparations for hair such as hair shampoo, hair rinses, hair treatments, hair conditioners, hair styling agents, and hair growth agents.

EXAMPLES

The present invention will be further illustrated in the following examples. However it is to be understood that these examples should not be used to limit the scope of the present invention in any manner. Unless otherwise noted, the blending amount of each component is expressed in mass % with respect to a system in which the component is blended.

Synthesis Example 1

Di(2-ethylhexyl)-4-methoxybenzalmalonate (i.e. the compound represented by the aforementioned formula (II))

0.02 mol of di 2-ethylhexyl malonate was dissolved into 5 mL of pyridine, and 0.02 mol of 4-methoxybenzaldehyde and 0.15 mL of piperidine were added thereto. The mixture was refluxed at 70 to 75° C. for 4.5 hours, and then cooled. The resulted solution was washed with 10 ml of water for twice, 10 ml of 1N hydrochloric acid for twice, and 10 ml of saturated sodium bicarbonate. The organic layer was dried with anhydrous sodium sulfate, and the solvent was distilled away to obtain the above-mentioned compound, di (2-ethylhexyl)-4-methoxybenzalmalonate, in a yellow oily liquid state (yield: 64%). The wavelength of maximum absorption of the compound was 310 nm and the absorbance was 0.56 (ethanol, 10 ppm). The absorption spectrum is shown in FIG. 1.

Test Example 2

Photoprotective Effect on Humane Body

The photoprotective effect on humane body was evaluated with use of the sample solutions (Samples 1 to 5) prepared in Test example 1. The in vivo SPF (i.e. in vivo Sun Protection Factor) and the in vivo PFA (i.e. in vivo Protection factor of UVA) of each sample solution was measured by a measurement method in accordance with COLIPA method. The result is shown in Table 1.

TABLE 1

| Components | Sample 1 | Sample 2 | Sample 3 | Sample 4 | Sample 5 |
|---|---|---|---|---|---|
| 4-tert-butyl-4'-methoxydibenzoylmethane [component (a)] | 2 | 2 | 2 | 2 | 2 |
| 2-ethylhexyl p-methoxycinnamate | — | — | — | 5 | 5 |
| Octocrylene [component (b)] | — | 5 | 5 | 5 | — |
| Di (2-ethylhexyl)-4-methoxybenzalmalonate [component (c)] | — | — | 3 | — | — |
| Trisodium edetate | 0.05 | 0.05 | 0.05 | 0.05 | 0.05 |
| Ethanol | 3 | 3 | 3 | 3 | 3 |
| Polyoxyethylene methyl glucoside | 1 | 1 | 1 | 1 | 1 |
| Decamethylcyclopentasiloxane | 30 | 30 | 30 | 30 | 30 |
| Dimethylpolysiloxane | 5 | 5 | 5 | 5 | 5 |
| Organic-modified montmorillonite | 0.2 | 0.2 | 0.2 | 0.2 | 0.2 |
| Polyoxyethylene/methylpolysiloxane copolymer | 1.5 | 1.5 | 1.5 | 1.5 | 1.5 |
| Octyl succinate | 5 | 5 | 5 | 5 | 5 |
| Antiseptic | 0.55 | 0.55 | 0.55 | 0.55 | 0.55 |
| Hydrophobized titanium dioxide | 10 | 10 | 10 | 10 | 10 |
| Purified water | residue | residue | residue | residue | residue |
| In vivo PFA | 3.0 | 10.2 | 10.2 | 5.7 | 5.7 |
| In vivo SPF | 10.0 | 23.6 | 44.5 | 37.0 | 20.0 |
| Residual ratio of component (a) after irradiation (%) (calculated by regarding the quantity of component (a) before irradiation as 100%) | 8.8 | 67.5 | 85.0 | 33.6 | 27.2 |

As is obvious from the absorption spectrum in FIG. 1, component (c) of the present invention has absorption maximum in the UV-B. In addition, it can be preferably blended into cosmetics because it has a good solubility in cosmetic bases such as alcohols, ester oils, and silicone oils. Particularly, the compound represented by the aforementioned formula (II) is an oily material and is excellent for use in cosmetics.

Test Example 1

Photostabilizing Effect

The following will describe how to prove that the effect of component (b) to photostabilize component (a) is not inhibited by the combined use of component (c).

Water-in-oil (W/O) type sunscreen compositions were prepared by a normal method according to the compositions in Table 1 below and used as sample solutions (namely, Samples 1 to 5). Samples 1 to 5 were applied to each membrane in 2 mg/cm² thickness evenly, and the membranes were irradiated by 280 to 800 nm wavelength at 40° C. for 2.5 hours with using the light source (Suntest™ Atlas Material Testing Technology LLC) which simulates sunlight.

The pre-irradiation and post-irradiation samples were individually soaked into 100 mL of tetrahydrofuran to extract UV absorber, and quantity of component (a) in each sample was determined by HPLC. A residual ratio of component (a) in each post-irradiation sample was calculated by regarding the quantity of component (a) in its pre-irradiation sample as 100%. The result is shown in Table 1.

As is obvious from the results in Table 1, Sample 3 containing components (a), (b), and (c), which is the composition of the present invention, achieves an excellent and improved photoprotective effect on human body and a photostabilizing effect as compared to Samples 1, 2, 4, and 5, which are the comparisons.

Test Example 3

Solubility of Poorly-Soluble UV Absorbers

Triazine derivative and dibenzoylmethane derivative (i.e. component (a)) were used as representative examples of poorly-soluble UV absorbers, and the solubility of each compound in the oils shown in Table 2 below was examined.

(Experimental Method)

Each of triazine derivative and dibenzoylmethane derivative was warmed and dissolved into each oil shown in Table 2, and then each mixture was cooled to room temperature. After adding crystal nuclei, they were cooled at 0° C. A saturation solubility of each supernatant fluid was measured. The result is shown in Table 2.

2,4-bis{[4-(2-ethylhexyloxy)-2-hydroxy]phenyl}-6-(4-methoxyphenyl) 1,3,5-triazine was used as triazine derivative.

4-tert-butyl-4'-methoxydibenzoylmethane was used as a dibenzoylmethane derivative (i.e. component (a)).

TABLE 2

| Oil | Saturation solubility of triazine derivative | Saturation solubility of dibenzoylmethane derivative |
| --- | --- | --- |
| Di (2-ethylhexyl)-4'-methoxybenzalmalonate [component (c)] | 8.8% | 10% |
| Alkyl benzoate (having a carbon number of 12 to 15) | 8% | 8.8% |
| Dioctyl succinate | 4% | 9.7% |
| Pentaerithrityl tetraoctanoate | 4% | 6% |

As is obvious from the results in Table 2, component (c) used in the present invention has similar or improved solubility in poorly-soluble UV absorbers, compared to the other oils having high solubility in poorly-soluble UV absorbers.

The formulation examples of the composition of the present invention will be described below.

Example 1

Sunscreen Emulsion (W/O)

| (Components) | (mass %) |
| --- | --- |
| A. Oil phase | |
| Volatile cyclic silicone | 27 |
| Dimethicone copolyol | 0.9 |
| Polyoxybutylene polyoxypropylene glycol ("UNIOL PB-700" produced by NOF CORPORATION) | 0.8 |
| Titanium dioxide (Hydrophobicized) | 10 |
| Zinc oxide (Hydrophobicized) | 10 |
| Talc (Hydrophobicized) | 4 |
| Phenethyl benzoate | 10 |
| 2-ethylhexyl p-methoxycinnamate | 3 |
| 4-methoxy-4'-t-butyldibenzoylmethane | 1 |
| 2,4-bis{[4-(2-ethylhexyloxy)-2-hydroxy]phenyl}-6-(4-methoxyphenyl)1,3,5-triazine | 1 |
| Octocrylene | 2 |
| 2-[4-(diethylamino)-2-hydroxybenzoyl]-benzoic acid hexyl ester | 1 |
| Di (2-ethylhexyl)-4-methoxybenzalmalonate | 1 |
| Organic-modified montmorillonite | 0.5 |
| Antiseptic | Q.S. |
| Perfume | Q.S. |
| B. Water phase | |
| 2-phenylbenzimidazole-5-sulfonic acid | 2 |
| Dipropylene glycol | 7 |
| Triethanolamine | 1.1 |
| Purified water | Balance |

(Preparation Method)

The components of the oil phase and those of the water phase were individually mixed and dissolved. In the oil phase, titanium dioxide was dispersed well, and then the water phase was added thereto. The mixture of the oil phase and the water phase was emulsified with a homogenizer. The obtained sunscreen emulsion had an extremely high photostability.

Example 2

Sunscreen Emulsion (W/O)

| (Components) | (mass %) |
| --- | --- |
| A. Oil phase | |
| Dimethylpolysiloxane | 1 |
| Decamethylcyclopentasiloxane | 25 |
| Trimethylsiloxysilicate | 5 |
| Polyoxyethylene/methylpolysiloxane copolymer | 1 |
| Lauryl PEG-9 polydimethylsiloxyethyl dimethicone | 1 |
| Isononyl isononanoate | 5 |
| 2-ethylhexyl p-methoxycinnamate | 3 |
| Dimethyl distearyl ammonium hectorite | 0.5 |
| Spherical polyalkyl acrylate powder | 5 |
| Butyl ethyl propanediol | 0.5 |
| 2,4,6-tris[p-(2'-ethylhexyl-1'-oxycarbonyl)anilino]1,3,5-triazine | 1 |
| Hydroxy-ethylhexylphenoxybenzotriazole | 1 |
| 4-methoxy-4'-t-butyldibenzoylmethane | 1 |
| 2,4-bis{[4-(2-ethylhexyloxy)-2-hydroxy]phenyl}-6-(4-methoxyphenyl)1,3,5-triazine | 2 |
| Octocrylene | 2 |
| 2-[4-(diethylamino)-2-hydroxybenzoyl]-benzoic acid hexyl ester | 1 |
| 2-phenylbenzimidazole-5-sulfonic acid | 1 |
| Di (2-ethylhexyl)-4-methoxybenzalmalonate | 3 |
| Alkyl-aryl-1,3-propanedione silicone | 5 |
| Phenethyl benzoate | 5 |
| Hydrophobized zinc oxide | 7 |
| Hydrophobized titanium dioxide | 8 |
| B. Water phase | |
| Sodium hydroxide | 0.15 |
| Dipropylene glycol | 5 |
| Dipotassium glycyrrhizinate | 0.02 |
| Glutathione | 1 |
| Thiotaurine | 0.05 |
| *Sophora angustifolia* extract | 1 |
| Paraben | Q.S. |
| Phenoxyethanol | Q.S. |
| Purified water | Balance |

(Preparation Method)

The water phase was gradually added to the oil phase. After completing the addition, a sunscreen emulsion was prepared with a mixer providing a uniform emulsified distribution of particles. The obtained sunscreen emulsion had an extremely high photostability.

Example 3

Sunscreen Cream (O/W)

| (Components) | (mass %) |
| --- | --- |
| A. Oil phase | |
| Stearic acid | 10 |
| Stearyl alcohol | 4 |
| Butyl stearate | 8 |
| Mono stearic acid ester of glycerin | 2 |
| Polyoxybutylene polyoxypropylene glycol ("UNIOL PB-700" produced by NOF CORPORATION) | 2 |
| Vitamin E acetate | 0.5 |

| (Components) | (mass %) |
|---|---|
| Vitamin A palmitate | 0.1 |
| Phenethyl benzoate | 5 |
| 4-methoxy-4'-t-butyldibenzoylmethane | 2 |
| 2,4-bis{[4-(2-ethylhexyloxy)-2-hydroxy]phenyl}-6-(4-methoxyphenyl)1,3,5-triazine | 3 |
| Octocrylene | 3 |
| 2-ethylhexyl p-methoxycinnamate | 3 |
| Di (2-ethylhexyl)-4-methoxybenzalmalonate | 3 |
| *Macadamia* nut oil | 1 |
| Tea seed oil | 3 |
| Perfume | 0.4 |
| Antiseptic | Q.S. |
| B. Water phase | |
| Glycerin | 4 |
| 1,2-pentadiol | 3 |
| Sodium hyaluronate | 1 |
| Potassium hydroxide | 2 |
| Magnesium ascorbyl phosphate | 0.1 |
| L-arginine hydrochloride | 0.01 |
| Trisodium edetate | 0.05 |
| Purified water | Balance |

(Preparation Method)

The components of the oil phase A and those of the water phase B were individually heated to 70° C. and dissolved completely. The oil phase A was added to the water phase B, and the mixture was emulsified with emulsification equipment. The product was cooled with a heat exchanger to obtain cream. The obtained sunscreen cream had an extremely high photostability.

Example 4

Cream (O/W)

| (Components) | (mass %) |
|---|---|
| A. Oil phase | |
| Cetanol | 4 |
| Petrolatum | 7 |
| Isopropyl myristate | 8 |
| Squalane | 10 |
| Octyl triazone | 2 |
| Di (2-ethylhexyl)-4-methoxybenzalmalonate | 1 |
| 2-ethylhexyl p-methoxycinnamate | 1 |
| Octocrylene | 0.5 |
| Butyl methoxydibenzoylmethane | 2 |
| Mono stearic acid ester of glycerin | 2.2 |
| POE(20) sorbitan monostearate | 2.8 |
| Phenethyl benzoate | 5 |
| Vitamin E nicotinate | 2 |
| Perfume | 0.3 |
| Antioxidants | Q.S. |
| Antiseptic | Q.S. |
| B. Water phase | |
| Glycerin | 10 |
| Sodium hyaluronate | 0.02 |
| Dipropylene glycol | 4 |
| Sodium pyrrolidone carboxylate | 1 |
| Disodium edetate | 0.01 |
| Purified water | Balance |

(Preparation Method)

The components of the oil phase and those of the water phase were individually mixed and dissolved. The water phase was added to the oil phase, and the mixture was emulsified with a homogenizer to obtain cream. The obtained cream had an extremely high photostability. Additionally, the cream achieved an excellent smoothness and a non-sticky feeling while it retained a moisturizing effect.

Example 5

Sunscreen Emulsion (O/W)

| (Components) | (mass %) |
|---|---|
| A. Oil phase | |
| Dimethicone copolyol | 0.5 |
| Decamethylcyclopentasiloxane | 15 |
| Isostearic acid | 0.5 |
| Phenyl trimethicone | 1 |
| Hydrophobized titanium oxide | 5 |
| 2,4,6-tris[p-(2'-ethylhexyl-1'-oxycarbonyl)anilino]1,3,5-triazine | 3 |
| 2-ethylhexyl p-methoxycinnamate | 5 |
| Alkyl-aryl-1,3-propanedione silicone derivative | 5 |
| 4-tert-butyl-4'-methoxydibenzoylmethane | 2 |
| Octocrylene | 0.5 |
| Di (2-ethylhexyl)-4-methoxybenzalmalonate | 2 |
| Silica | 1 |
| Phenoxyethanol | Q.S. |
| Glycerin | 1 |
| Succinoglycan | 0.2 |
| Cellulose gum | 1 |
| Phenethyl benzoate | 5 |
| B. Water phase | |
| Polyoxyethylene hardened castor oil | 1 |
| Citric acid | 0.01 |
| Sodium citrate | 0.09 |
| Paraben | Q.S. |
| Ethanol | 5 |
| Ion-exchanged water | Balance |

(Preparation Method)

The components of the oil phase and those of the water phase were individually mixed and dissolved. The oil phase was added to the water phase, and the mixture was emulsified with a homogenizer to obtain a sunscreen emulsion. The obtained sunscreen emulsion had an extremely high photostability.

What is claimed is:

1. A composition for skin or hair comprising;
   (a) 0.01 to 10% by mass of a dibenzoylmethane derivative with respect to the composition,
   (b) 0.01 to 10% by mass of an alkyl β,β-diphenylacrylate and/or α-cyano-β,β-diphenylacrylate with respect to the composition, and
   (c) 0.1% by mass or more of a benzalmalonate derivative with respect to the composition represented by the following formula (I):

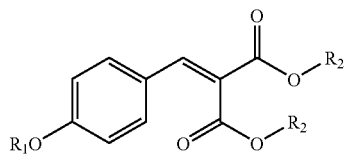

(I)

wherein, $R_1$ and $R_2$ independently represent an alkyl group having a carbon number of 1 to 20.

2. The composition for skin or hair according to claim 1, wherein $R_1$ is a methyl group.

3. The composition for skin or hair according to claim 1 wherein $R_2$ is a 2-ethylhexyl group.

4. The composition for skin or hair according to claim 1 wherein component (a) is 4-tert-butyl-4'-methoxydibenzoyl-methane.

5. The composition for skin or hair according to claim 1 wherein component (b) is octocrylene.

6. A sunscreen cosmetic comprising the composition of claim 1.

7. The composition for skin or hair according to claim 2 wherein $R_2$ is a 2-ethylhexyl group.

8. The composition for skin or hair according to claim 2 wherein component (a) is 4-tert-butyl-4'-methoxydibenzoyl-methane.

9. The composition for skin or hair according to claim 3 wherein component (b) is octocrylene.

10. A sunscreen cosmetic comprising the composition of claim 2.

11. The composition for skin or hair according to claim 3 wherein component (a) is 4-tert-butyl-4'-methoxydibenzoyl-methane.

12. The composition for skin or hair according to claim 4 wherein component (b) is octocrylene.

13. The composition for skin or hair according to claim 1, wherein the benzalmalonate derivative is di(2-ethylhexyl)-4-methoxybenzalmalonate.

* * * * *